(12) United States Patent
Palatnik et al.

(10) Patent No.: US 6,781,034 B2
(45) Date of Patent: Aug. 24, 2004

(54) STRESS TOLERANT PLANTS

(75) Inventors: Javier F. Palatnik, Rosario (AR);
Maria F. Fillat Castejon, Zaragoza (ES); Nestor J. Carrillo, V.G. Galvez (AR); Estela M. Valle, Rosario (AR); Vanesa S. Tognetti, Rosario (AR)

(73) Assignee: Plant Bioscience Limited, Norwich (GB)

( * ) Notice: Subject to any disclaimer, the term of this patent is extended or adjusted under 35 U.S.C. 154(b) by 81 days.

(21) Appl. No.: 09/983,536

(22) Filed: Oct. 24, 2001

(65) Prior Publication Data

US 2003/0093833 A1 May 15, 2003

(51) Int. Cl.[7] .................. C12N 15/82; C12N 15/70; C12N 15/90; A01H 1/00

(52) U.S. Cl. .................. 800/288; 435/69.8; 435/320.1; 435/419; 435/468; 435/471; 800/260

(58) Field of Search .................. 435/69.1, 320.1, 435/69.7, 69.8, 410, 419, 468, 471; 800/278, 288, 298, 295, 260

(56) References Cited

PUBLICATIONS

Paltnik et al., Plant Physiol., 1997, vol. 115, pp. 1721–1727.*
Dupree et al. , Curr. Res. Photosyn. 1990, vol. III, pp. 625–628.*
Espinosa–Ruiz et al, "*Arabidopsis thaliana* AtHAL3: a flavoprotein related to salt and osmotic tolerance and plant growth", Plant Journal 20(5):529–539 (1999).
Lin Chentao et al, "Expression of an Arabidopsis cryptochrome gene in transgenic tobacco results in hypersensitivity to blue. UV–A, and green light", PNAS 92(18):8423–8427 (1995).
Kitamura Masaya et al, "Cloning and expression of the gene encoding flavodoxin from *Desulfovibrio vulgaris* (Miyazaki F)", Journal of Biochemistry 123(5):891–898 (1998).

* cited by examiner

*Primary Examiner*—Ashwin Mehta
(74) *Attorney, Agent, or Firm*—Nixon & Vanderhye P.C.

(57) ABSTRACT

The present invention relates to the finding that the accumulation of flavodoxin within chloroplasts of plant cells provides enhanced resistance to sources of environmental stress, including ultraviolet AB radiation, extreme temperatures, infection and/or high doses of irradiation. Nucleic acids encoding flavodoxin fused to a chloroplast targeting peptide, cells, plants and methods pertaining thereto are described.

24 Claims, 6 Drawing Sheets

GGATCCATCATCAACAACAACAACAAACATGGCTGCTGCAGTAACAGCCGCAGTCTC

CTTGCCATACTCCAACTCCACTTCCCTTCCGATCAGAACATCTATTGTTGCACCAGA

GAGACTTGTCTTCAAAAAGGTTTCATTGAACAATGTTTCTATAAGTGGAAGGGTAGG

CACCATCAGAGCTCTCATAATGTCAAAGAAAATTGGTTTATTCTACGGTACTCAAAC

TGGTAAAACTGAATCAGTAGCAGAAATCATTCGAGACGAGTTTGGTAATGATGTGGT

GACATTACACGATGTTTCCCAGGCAGAAGTAACTGACTTGAATGATTATCAATATTT

GATTATTGGCTGTCCTACTTGGAATATTGGCGAACTGCAAAGCGATTGGGAAGGACT

CTATTCAGAACTGGATGATGTAGATTTTAATGGTAAATTGGTTGCCTACTTTGGGAC

TGGTGACCAAATAGGTTACGCAGATAATTTTCAGGATGCGATCGGTATTTTGGAAGA

AAAAATTTCTAACGTGGTGGTAAAACTGTCGGCTATTGGTCAACTGATGGATATGA

TTTTAATGATTCCAAGGCACTAAGAAATGGCAAGTTTGTAGGACTAGCTCTTGATGA

AGATAATCAATCTGACTTAACAGACGATCGCATCAAAAGTTGGGTTGCTCAATTAAA

GTCTGAATTTGGTTTGTAAAAA

ATGGCTGCTGCAGTAACAGCCGCAGTCTCCTTGCCATACTCCAACTCCACTTCCCTT

CCGATCAGAACATCTATTGTTGCACCAGAGAGACTTGTCTTCAAAAAGGTTTCATTG

AACAATGTTTCTATAAGTGGAAGGGTAGGCACCATCAGAGCTCTCATA

SEQUENCE LISTING

```
<160> NUMBER OF SEQ ID NOS: 6

<210> SEQ ID NO 1
<211> LENGTH: 706
<212> TYPE: DNA
<213> ORGANISM: Artificial Sequence
<220> FEATURE:
<223> OTHER INFORMATION: Description of Artificial Sequence: Nucleic
      acid molecule encoding fusion polypeptide

<400> SEQUENCE: 1
ggatccatca tcaacaacaa caacaaacat ggctgctgca gtaacagccg cagtctcctt      60
gccatactcc aactccactt cccttccgat cagaacatct attgttgcac cagagagact     120
tgtcttcaaa aaggtttcat tgaacaatgt ttctataagt ggaagggtag gcaccatcag     180
agctctcata atgtcaaaga aaattggttt attctacggt actcaaactg gtaaaactga     240
atcagtagca gaaatcattc gagacgagtt tggtaatgat gtggtgacat tacacgatgt     300
ttcccaggca gaagtaactg acttgaatga ttatcaatat ttgattattg gctgtcctac     360
ttggaatatt ggcgaactgc aaagcgattg ggaaggactc tattcagaac tggatgatgt     420
agattttaat ggtaaattgg ttgcctactt tgggactggt gaccaaatag gttacgcaga     480
taattttcag gatgcgatcg gtattttgga agaaaaaatt tctcaacgtg gtggtaaaac     540
tgtcggctat tggtcaactg atggatatga ttttaatgat tccaaggcac taagaaatgg     600
caagtttgta ggactagctc ttgatgaaga taatcaatct gacttaacag acgatcgcat     660
caaaagttgg gttgctcaat taaagtctga atttggtttg taaaaa                    706

<210> SEQ ID NO 2
<211> LENGTH: 233
<212> TYPE: PRT
<213> ORGANISM: Artificial Sequence
<220> FEATURE:
<223> OTHER INFORMATION: Description of Artificial Sequence: Predicted
      protein sequence of transit peptide and flavodoxin
      protein
```

<400> SEQUENCE: 2

Asp Pro Ser Ser Thr Thr Thr Asn Met Ala Ala Val Thr Ala
1               5                   10                  15

Ala Val Ser Leu Pro Tyr Ser Asn Ser Thr Ser Leu Pro Ile Arg Thr
            20                  25                  30

Ser Ile Val Ala Pro Glu Arg Leu Val Phe Lys Lys Val Ser Leu Asn
            35                  40                  45

Asn Val Ser Ile Ser Gly Arg Val Gly Thr Ile Arg Ala Leu Ile Met
        50                  55                  60

Ser Lys Lys Ile Gly Leu Phe Tyr Gly Thr Gln Thr Gly Leu Thr Glu
65                  70                  75                  80

Ser Val Ala Glu Ile Ile Arg Asp Glu Phe Gly Asn Asp Val Val Thr
                85                  90                  95

Leu His Asp Val Ser Gln Ala Glu Val Thr Asp Leu Asn Asp Tyr Gln
            100                 105                 110

Tyr Leu Ile Ile Gly Cys Pro Thr Trp Asn Ile Gly Glu Leu Gln Ser
            115                 120                 125

Asp Trp Glu Gly Leu Tyr Ser Glu Leu Asp Asp Val Asp Phe Asn Gly
130                 135                 140

Lys Leu Val Ala Tyr Phe Gly Thr Gly Asp Gln Ile Gly Tyr Ala Asp
145                 150                 155                 160

Asn Phe Gln Asp Ala Ile Gly Ile Leu Glu Glu Lys Ile Ser Gln Arg
                165                 170                 175

Gly Gly Lys Thr Val Gly Tyr Trp Ser Thr Asp Gly Tyr Asp Phe Asn
            180                 185                 190

Asp Ser Lys Ala Leu Arg Asn Gly Lys Phe Val Gly Leu Ala Leu Asp
        195                 200                 205

Glu Asp Asn Gln Ser Asp Leu Thr Asp Asp Arg Ile Lys Ser Trp Val
    210                 215                 220

Ala Gln Leu Lys Ser Glu Phe Gly Leu
225                 230

<210> SEQ ID NO 3
<211> LENGTH: 162
<212> TYPE: DNA
<213> ORGANISM: Pisum sativum

<400> SEQUENCE: 3
atggctgctg cagtaacagc cgcagtctcc ttgccatact ccaactccac ttcccttccg      60
atcagaacat ctattgttgc accagagaga cttgtcttca aaaggtttc attgaacaat      120 gtttctataa gtggaagggt aggcaccatc agagctctca ta                        162

<210> SEQ ID NO 4
<211> LENGTH: 54
<212> TYPE: PRT
<213> ORGANISM: Pisum sativum

<400> SEQUENCE: 4

Met Ala Ala Ala Val Thr Ala Ala Val Ser Leu Pro Tyr Ser Asn Ser
1               5                   10                  15

Thr Ser Leu Pro Ile Arg Thr Ser Ile Val Ala Pro Glu Arg Leu Val
            20                  25                  30

Phe Lys Lys Val Ser Leu Asn Asn Val Ser Ile Ser Gly Arg Val Gly
        35                  40                  45

-continued

```
Thr Ile Arg Ala Leu Ile
    50

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 5
gacgagctct cataatgtca aag                                               23

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 6
actgtcgact ttttacaaac caaat                                             25
```

STRESS TOLERANT PLANTS

The present invention relates to methods for improving environmental stress tolerance of plants and plants with such improved stress tolerance. More particularly, the invention relates to the finding that the expression of a flavoprotein such as flavodoxin within plant cells is beneficial to plants which are subjected to environmental stress.

BACKGROUND OF THE INVENTION

Environmental stress is a major limiting factor for plant productivity and crop yield. Many of the deleterious processes undergone by plants exposed to adverse environmental conditions are mediated by reactive oxygen species (ROS) which are generated in chloroplasts through the faulty performance of the photosynthetic apparatus (Foyer, C. H. et al. (1994) Plant Cell Environ. 17,507–523, Hammond-Kosack, K. E., and Jones, J. D. G. (1996) Plant Cell 8, 1773–1791, Allen, R. (1995) Plant Physiol. 107, 1049–1054).

Auto-oxidation of components of the photosynthetic electron transport chain leads to the formation of superoxide radicals and their derivatives, hydrogen peroxide and hydroxyl radicals. These compounds react with a wide variety of biomolecules (most conspicuously, DNA), causing cell stasis and death.

To cope with the damaging effects of reactive oxygen species (ROS), aerobic organisms have evolved highly efficient antioxidant defense systems which are made up of both enzymatic and non-enzymatic constituents. In different tissues and organisms, antioxidants play different and often complementary protective functions, such as direct scavenging of ROS, replacement of damaged oxidant sensitive biomolecules and DNA repair activities (Fridovich, I. (1997). J. Biol. Chem. 272,1851–1857). At least part of the cellular response against oxidative stress is of an adaptive nature and involves de novo synthesis of committed members of the antioxidant barrier. Various multigenic responses have been recognized in the facultative aerobic bacterium *Escherichia coli*, including those modulated by the soxRS and oxyR regulons (Hidalgo, E., and Demple, B. (1996). In Regulation of Gene Expression in *Escherichia coli*, Molecular Biology Intelligence Unit Series (E. C. C. Lin and A. S. Lynch, eds.), pp. 434–452, Austin, Tex.: R. G. Landis).

The soxRS response appears to be specifically tailored to face the challenges imposed by exposure of the cells to superoxide radicals or to nitric oxide. Many different components of the response have been identified, including two soluble flavoproteine: FAD-containing ferredoxin-NADP+ reductase (FNR), and its electron partner substrate flavodoxin (Liochev et al. (1994) Proc. Natl Acad. Sci. U.S. Pat. No. 91,1328–1331, Zheng, M. et al (1999) J. Bacteriol. 181,4639–4643).

Flavodoxins are small monomeric proteins (Mw 18,800) containing one molecule of non-covalently bound FMN (Razquin, P. et al (1988) J. Bacteriol. 176, 7409–7411). FNR is able to use, with roughly similar efficiencies, both flavodoxin and the iron-sulfur protein ferredoxin as substrates for its NADP(H) oxidoreductase activity. In cyanobacteria, flavodoxin expression is induced under conditions of iron deprivation, when ferredoxin cannot be synthesized.

As part of the soxRS response of *E. coli*, both FNR and flavodoxin levels increase over twenty times upon treatment of the bacteria with superoxide-propagating compounds such as the redox cycling herbicide methyl viologen (MV), whereas ferredoxin amounts are not affected (Rodriguez, R. E. et al (1998) Microbiology 144,2375–2376). Unlike FNR and ferredoxins, which are widely distributed among plastids, mitochondria and bacteria, flavodoxin occurrence appears to be largely restricted to bacteria. Flavodoxins have not been isolated from plant tissues, and no flavodoxin homologue has been recognized in the *Arabidopsis thaliana* genome (The Arabidopsis Genome Initiative (2000) Nature 408,796–815).

The present invention relates to the finding that plant lines which have been engineered to express a flavoprotein such as flavodoxin display highly enhanced tolerance compared to control, untreated plants, when exposed to a plethora of adverse environmental conditions.

SUMMARY OF THE INVENTION

In various aspects, the present invention provides nucleic acids and vectors suitable for use in methods of producing stress tolerant plants. In preferred embodiments, such nucleic acids and vectors provide for the accumulation of flavoprotein within the choloroplasts of plant cells transformed therewith. In some embodiments of the invention, accumulation within the chloroplasts is achieved by fusing the flavoprotein to a chloroplast targeting polypeptide.

A first aspect of the present invention provides an isolated nucleic acid encoding a fusion polypeptide comprising a flavoprotein polypeptide and a chloroplast targeting peptide.

A nucleic acid may encode a fusion polypeptide comprising a flavoprotein polypeptide and a chloroplast targeting peptide.

A flavodoxin polypeptide may be a bacterial flavodoxin polypeptide, for example a cyanobacterial flavodoxin polypeptide such as the flavodoxin of the cyanobacterium Anabaena PCC7119 (Fillat M. et al (1991) Biochem J. 280 187–191). Other suitable flavodoxin polypeptides include flavodoxins from photosynthetic anoxigenic bacteria, enterobacteria, diazotrophs and algae. Examples of flavodoxin polypeptides suitable for use according to the present invention are exemplified in Table 1. Whilst a wild type flavodoxin polypeptide is preferred, a flavodoxin polypeptide may also be a fragment, mutant, derivative, variant or allele of such a wild type sequence.

Suitable fragments, mutants, derivatives, variants and alleles are those which encode a protein which retain the functional characteristics of the polypeptide encoded by the wild-type flavoprotein gene, especially the ability to act as an anti-oxidant. Changes to a sequence, to produce a mutant, variant or derivative, may be by one or more of addition, insertion, deletion or substitution of one or more nucleotides in the nucleic acid, leading to the addition, insertion, deletion or substitution of one or more amino acids in the encoded polypeptide. Of course, changes to the nucleic acid which make no difference to the encoded amino acid sequence are included.

Flavodoxin polypeptides are monomeric hydrophillic flavoproteins of a molecular mass of less than 20 kDa, containing one mole of non covalently bound flavin mononucleotide (FMN) per molecule of apoprotein. The flavin group can be reversibly dissociated by mild acid treatment.

Flavodoxin polypeptides engage in one-electron transfer reactions with several electron partners such as FNR, pyruvate-flavodoxin reductase and photosystems, replacing ferredoxin in most of its activities. Even though flavodoxin can in principle exchange two electrons, it behaves as an obligatory one-electron carrier. Contrary to other flavoproteins, the half-reduced semiquinone and the fully reduced hydroquinone are the most stable species, and these are the forms relevant for flavodoxin functions.

A polypeptide which is a member of the Flavodoxin family or which is an amino acid sequence variant, allele, derivative or mutant thereof may comprise an amino acid sequence which shares greater than about 30% sequence identity with the sequence of Anabaena PCC7119 flavodoxin, greater than about 35%, greater than about 40%, greater than about 45%, greater than about 55%, greater than about 65%, greater than about 70%, greater than about 80%, greater than about 90% or greater than about 95%. The sequence may share greater than about 30% similarity with Anabaena PCC7119 flavodoxin, greater than about 40% similarity, greater than about 50% similarity, greater than about 60% similarity, greater than about 70% similarity, greater than about 80% similarity or greater than about 90% similarity.

In certain embodiments, a flavodoxin polypeptide may show little overall homology, say about 20%, or about 25%, or about 30%, or about 35%, or about 40% or about 45%, with the Anabaena PCC7119 flavodoxin sequence, even though it possesses the same anti-oxidation activity. However, in functionally significant domains or regions, the amino acid homology may be much higher. For example, a flavodoxin polypeptide comprises an FMN-binding domain which has high homology to the flavodoxin FMN binding domain (a flavodoxin-like domain). Putative functionally significant domains or regions can be identified using processes of bioinformatics, including comparison of the sequences of homologues.

Sequence similarity and identity is commonly defined with reference to the algorithm GAP (Genetics Computer Group, Madison, Wis.). GAP uses the Needleman and Wunsch algorithm to align two complete sequences that maximizes the number of matches and minimizes the number of gaps. Generally, default parameters are used, with a gap creation penalty=12 and gap extension penalty=4.

Use of GAP may be preferred but other algorithms may be used, e.g. BLAST (which uses the method of Altschul et al. (1990) *J. Mol. Biol.* 215: 405–410), FASTA (which uses the method of Pearson and Lipman (1988) *PNAS USA* 85: 2444–2448), or the Smith-Waterman algorithm (Smith and Waterman (1981) *J. Mol Biol.* 147: 195–197), or the TBLASTN program, of Altschul et al. (1990) supra, generally employing default parameters. In particular, the psi-Blast algorithm (Nucl. Acids Res, (1997) 25 3389–3402) may be used.

Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine. Particular amino acid sequence variants may differ from a known flavodoxin polypeptide sequence as described herein by insertion, addition, substitution or deletion of 1 amino acid, 2, 3, 4, 5–10, 10–20 20–30, 30–50, or more than 50 amino acids.

Sequence comparison may be made over the full-length of the relevant sequence described herein, or may more preferably be over a contiguous sequence of about or greater than about 20, 25, 30, 33, 40, 50, 70, 120, 170 or more amino acids or nucleotide triplets, compared with the relevant amino acid sequence or nucleotide sequence as the case may be.

Other methods suitable for use in identifying flavodoxin polypeptides are well-known in the art.

In other embodiments, the isolated nucleic acid may encode a fusion polypeptide which comprises an FNR polypeptide and a heterogeneous chloroplast targeting peptide.

Many ferredoxin-NADP(+) reductase (FNR) polypeptides are known in the art and an FNR polypeptide suitable for use in accordance with embodiments of the present invention may readily identified by a skilled person. Other suitable FNR polypeptides may be found on the NCBI database at www(dot)ncbi(dot)nlm(dot)nih(dot)gov (forward slash)entrez(forward slash), for example, FNR polypeptide sequences having database accession numbers NP 418359, NP 312876, P28861, and AAG59117. Suitable PNR polypeptides have the anti-oxidant and electron transfer activity of wild type ferredoxin-NADP(+) reductase.

A chloroplast targeting peptide suitable for use in accordance with certain embodiments of the present invention may be any peptide sequence which directs a polypeptide to the chloroplast of a plant cell. Suitable peptides may readily be identified by a skilled person and some examples are shown in Table 2. Other examples may be found on the NCBI database (www(dot)ncbi(dot)nlm(dot)nih(dot)gov (forward slash)entrez(forward slash)). In some preferred embodiments, a peptide may have the chloroplast transit polypeptide of the pea FNR, which has the sequence shown in FIG. 6.

In other embodiments of the present invention, flavoprotein may accumulate within chloroplasts as a result of expression within the chloroplast of nucleic acid encoding the polypeptide following direct transformation of the chloroplast. There is no requirement for a targeting or transit peptide in such embodiments.

Particle bombardment methods (Ruf, S. et al. (2001) *Nature Biotechnol.* 19, 870–875) are particularly suitable for direct chloroplast transformation. With suitable plant regulatory elements, the transformed DNA may be transcribed within the plastid and translated into polypeptide in stromal ribosomes.

A nucleic acid encoding any flavoprotein polypeptide as defined above may be used in accordance with the present invention with any suitable chloroplast targeting peptide as defined above. The particular choice of flavoprotein polypeptide and targeting peptide is not critical to the practice of the present invention. Preferably, the flavoprotein polypeptide is not fused to a targeting peptide with which it is naturally associated i.e. it is fused to a heterogeneous targeting polypeptide. Flavodoxin polypeptides, which are not found in plants, are not naturally associated with chloroplast targeting signals.

In some preferred embodiments, a fusion polypeptide comprising a flavodoxin polypeptide and a chloroplast targeting peptide may have the sequence shown in FIG. 4. A suitable nucleic acid molecule encoding such a fusion polypeptide may have the sequence shown in FIG. 3.

The present invention also provides a nucleic acid construct or vector which comprises a nucleic acid encoding a fusion polypeptide comprising a flavodoxin polypeptide and a chloroplast targeting peptide, preferably a construct or vector from which the fusion polypeptide encoded by the nucleic acid sequence can be expressed. The construct or vector is preferably suitable for transformation into and/or expression within a plant cell.

A construct or vector comprising nucleic acid according to this aspect of the present invention need not include a promoter or other regulatory sequence, particularly if the vector is to be used to introduce the nucleic acid into cells for recombination into the genome.

However, in one aspect the present invention provides a nucleic acid construct comprising a nucleic acid sequence encoding a flavodoxin polypeptide operably linked to a plant specific regulatory sequence, such as a promoter. Such constructs are particularly useful in embodiments in which chloroplasts are directly transformed with nucleic acid, which is subsequently expressed therein under the control of the plant specific regulatory element.

A plant specific regulatory sequence or element is a sequence which preferentially directs the expression (i.e. transcription) of a nucleic acid within a plant cell relative to other cell types. For example, expression from such a sequence is reduced or abolished in non-plant cells, such as bacterial or mammalian cells. A suitable regulatory sequence may for example be derived from a plant virus such as Cauliflower Mosaic Virus 35S. A regulatory sequence may be inducible, as described further below. The present invention also encompasses vectors comprising such a nucleic acid sequence.

Another aspect of the present invention provides the use of a nucleic acid as described herein in the production of a transgenic plant. Such a method may be for improving the tolerance of a plant to stress, in particular environmental stress, such as oxidative stress. Such stress may be biotic, abiotic or xenobiotic in nature and may include herbicide exposure, ultraviolet AB radiation, extreme temperatures, infection, for example with a necrotizing pathogen such as a bacterium or fungus and/or high doses of irradiation.

Nucleic acid may of course be double- or single-stranded, cDNA or genomic DNA, or RNA. The nucleic acid may be wholly or partially synthetic, depending on design. Naturally, the skilled person will understand that where the nucleic acid according to the invention includes RNA, reference to the sequence shown should be construed as reference to the RNA equivalent, with U substituted for T. The present invention also encompasses the expression product of any of the nucleic acid sequences disclosed and methods of making the expression product by expression from encoding nucleic acid therefore under suitable conditions in suitable host cells.

Those skilled in the art are well able to construct vectors and design protocols for recombinant gene expression, for example in a microbial or plant cell. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual*: 2nd edition, Sambrook et al, 1989, Cold Spring Harbor Laboratory Press.

Many known techniques and protocols for manipulation of nucleic acid, for example in preparation of nucleic acid constructs, mutagenesis, sequencing, introduction of DNA into cells and gene expression, and analysis of proteins, are described in detail in *Protocols in Molecular Biology*, Second Edition, Ausubel et al. eds., John Wiley & Sons, 1992. Specific procedures and vectors previously used with wide success upon plants are described by Bevan, Nucl. Acids Res. (1984) 12, 8711–8721), and Guerineau and Mullineaux, (1993) Plant transformation and expression vectors. In: Plant Molecular Biology Labfax (Croy RRD ed) Oxford, BIOS Scientific Publishers, pp 121–148.

A nucleic acid sequence as described herein, for example a sequence encoding a flavodoxin polypeptide, may be under operative control of a regulatory sequence active in plants for control of expression. It is indeed preferred that the coding sequence is operably linked to one or more regulatory sequences which may be heterologous or foreign to the gene (i.e. a non-bacterial sequence), for example a plant regulatory sequence. Such regulatory sequences may provide for efficient expression within a plant cell.

The term "heterologous" may be used to indicate that the gene/sequence of nucleotides in question have been introduced into said cells of the plant or an ancestor thereof, using genetic engineering or recombinant means, i.e. by human intervention. Nucleotide sequences heterologous, or exogenous or foreign, to a plant cell may be non-naturally occurring in cells of that type, variety or species. For example, there are no reports of flavodoxins in plant cells and nucleic acid encoding a flavodoxin polypeptide is therefore "heterologous" to a plant cell transformed therewith.

A nucleic acid construct which comprises a nucleic acid sequence encoding a flavoprotein such as flavodoxin, may include an inducible promoter operatively linked to the nucleic acid sequence. Such a promoter may be a stress inducible promoter. As discussed, this allows control of expression, for example, in response to an environmental stress. The invention also provides plants transformed with said gene construct and methods including introduction of such a construct into a plant cell and/or induction of expression of a construct within a plant cell, e.g. by application of a suitable stimulus, which may be an environmental stress stimulus such as a change in external conditions.

The term "inducible" as applied to a promoter is well understood by those skilled in the art. In essence, expression under the control of an inducible promoter is "switched on" or increased in response to an applied stimulus (which may be generated within a cell or provided exogenously). The nature of the stimulus varies between promoters. Whatever the level of expression is in the absence of the stimulus, expression from any inducible promoter is increased in the presence of the correct stimulus The preferable situation is where the level of expression increases upon in the presence of the relevant stimulus by an amount effective to alter a phenotypic characteristic i.e. to enhance stress tolerance. Thus an inducible (or "switchable") promoter may be used which causes a basic level of expression in the absence of the stimulus which level is too low to bring about the desired stress tolerant phenotype (and may in fact be zero). Upon application of the stimulus, which may for example, be an increase in environmental stress, expression is increased (or switched on) to a level which causes enhanced stress tolerance.

Many examples of inducible promoters will be known to those skilled in the art.

Other suitable promoters may include the Cauliflower Mosaic Virus 35S (CaMV 35S) gene promoter that is expressed at a high level in virtually all plant tissues (Benfey et al, (1990) EMBO J 9: 1677–1684); the cauliflower meri 5 promoter that is expressed in the vegetative apical meristem as well as several well localised positions in the plant body, e.g. inner phloem, flower primordial branching points in root and shoot (Medford, J. I. (1992) *Plant Cell* 4, 1029–1039; Medford et al, (1991) *Plant Cell* 3, 359–370) and the *Arabidopsis thaliana* LEAFY promoter that is expressed very early in flower development (Weigel et al, (1992) *Cell* 69, 843–859).

Constructs and vectors may further comprise selectable genetic markers consisting of chimaeric genes that confer selectable phenotypes such as resistance to antibiotics such as kanamycin, hygromycin, phosphinotricin, chlorsulfuron, methotrexate, gentamycin, spectinomycin, imidazolinones and glyphosate.

When introducing a chosen gene construct into a cell, certain considerations must be taken into account, well known to those skilled in the art. The nucleic acid to be inserted should be assembled within a construct which contains effective regulatory elements which will drive transcription. There must be available a method of transporting the construct into the cell. Once the construct is within the cell membrane, integration into the endogenous chromosomal material either will or will not occur. Finally, as far as plants are concerned, the target cell type must be such that cells can be regenerated into whole plants.

Techniques well known to those skilled in the art may be used to introduce nucleic acid constructs and vectors into plant cells to produce transgenic plants of the appropriate stress tolerant phenotype.

Agrobacterium transformation is one method widely used by those skilled in the art to transform dicotyledonous species. Production of stable, fertile transgenic plants in almost all economically relevant monocot plants is also now routine:(Toriyama, et al. (1988) *Bio/Technology* 6, 1072–1074; Zhang, et al. (1988) *Plant Cell Rep.* 7, 379–384; Zhang, et al. (1988) *Theor Appl Genet* 76, 835–840; Shimamoto, et al (1989) *Nature* 338, 274–276; Datta, et al. (1990) *Bio/Technology* 8, 736–740; Christou, et al. (1991) *Bio/Technology* 9, 957–962; Peng, et al. (1991) International Rice Research Institute, Manila, Philippines 563–574; Cao, et al. (1992) *Plant Cell Rep.* 11, 585–591; Li, et al. (1993) *Plant Cell Rep.* 12, 250–255; Rathore, et al. (1993) *Plant Molecular Biology* 21, 871–884; Fromm, et al. (1990) *Bio/Technology* 8, 833–839; Gordon-Kamm, et al. (1990) *Plant Cell* 2, 603–618; D'Halluin, et al. (1992) *Plant Cell* 4, 1495–1505; Walters, et al. (1992) *Plant Molecular Biology* 18, 189–200; Koziel, et al. (1993) *Biotechnology* 11, 194–200; Vasil, I. K. (1994) *Plant Molecular Biology* 25, 925–937; Weeks, et al. (1993) *Plant Physiology* 102, 1077–1084; Somers, et al. (1992) *Bio/Technology* 10, 1589–1594; WO92/14828). In particular, Agrobacterium mediated transformation is now a highly efficient alternative transformation method in monocots (Hiei et al. (1994) *The Plant Journal* 6, 271–282).

The generation of fertile transgenic plants has been achieved in the cereals rice, maize, wheat, oat, and barley (reviewed in Shimamoto, K. (1994) *Current Opinion in Biotechnology* 5, 158–162.; Vasil, et al. (1992) *Bio/Technology* 10, 667–674; Vain et al., 1995, *Biotechnology Advances* 13 (4): 653–671; Vasil, 1996, *Nature Biotechnology* 14 page 702). Wan and Lemaux (1994) *Plant Physiol.* 104: 37–48 describe techniques for generation of large numbers of independently transformed fertile barley plants.

Other methods, such as microprojectile or particle bombardment (U.S. Pat. No. 5,100,792, EP-A-444882, EP-A-434616), electroporation (EP 290395, WO 8706614)), microinjection (WO 92/09696, WO 94/00583, EP 331083, EP 175966, Green et al. (1987) *Plant Tissue and Cell Culture*, Academic Press) direct DNA uptake (DE 4005152, WO 9012096, U.S. Pat. No. 4,684,611), liposome mediated DNA uptake (e.g. Freeman et al. *Plant Cell Physiol.* 29: 1353 (1984)), or the vortexing method (e.g. Kindle, *PNAS U.S.A.* 87: 1228 (1990d)) may be preferred where Agrobacterium transformation is inefficient or ineffective.

Physical methods for the transformation of plant cells are reviewed in Oard, 1991, *Biotech. Adv.* 9: 1–11.

Alternatively, a combination of different techniques may be employed to enhance the efficiency of the transformation process, e.g. bombardment with Agrobacterium coated microparticles (EP-A-486234) or microprojectile bombardment to induce wounding followed by co-cultivation with Agrobacterium (EP-A-486233).

Following transformation, a plant may be regenerated, e.g from single cells, callus tissue or leaf discs, as is standard in the art. Almost any plant can be entirely regenerated from cells, tissues and organs of the plant. Available techniques are reviewed in Vasil et al., *Cell Culture and Somatic Cell Genetics of Plants, Vol I, II and III, Laboratory Procedures and Their Applications*, Academic Press, 1984, and Weissbach and Weissbach, *Methods for Plant Molecular Biology*, Academic Press, 1989.

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention, nor is the choice of technique for plant regeneration.

A further aspect of the present invention provides a method of producing a cell which includes incorporating an isolated nucleic acid sequence encoding a flavoprotein polypeptide such as a flavodoxin polypeptide or an FNR polypeptide or a nucleic acid vector comprising such a sequence into the cell by means of transformation. Such a method of producing a cell may include recombining the nucleic acid with the cell genome nucleic acid such that it is stably incorporated therein. A plant may be regenerated from one or more cells transformed as described.

The flavoprotein polypeptide, the encoding nucleic acid, and/or the vector comprising the nucleic acid are preferably heterogeneous i.e. exogenous or foreign to the plant cell transformed therewith.

A method of producing a plant cell may include expressing the nucleic acid and causing or allowing the accumulation of flavoprotein polypeptide expressed thereby in the chloroplast-of said plant cell.

A suitable flavoprotein polypeptide for use in such methods may be an FNR polypeptide or a flavodoxin polypeptide.

A method of making such a plant cell may include the introduction of such a nucleotide sequence or a suitable vector including the sequence into a plant cell and causing or allowing recombination between the vector and the plant cell genome to introduce the nucleic acid sequence into the genome.

A method may further include sexually or asexually propagating or growing off-spring or a descendant of the plant regenerated from said plant cell.

The invention further encompasses a host cell transformed with a nucleic acid sequence or vector as set forth above, i.e. containing a nucleic acid or vector as described above, especially a plant cell, for example a higher plant cell, or a microbial cell. Thus, a host cell, such as a plant cell, including a nucleotide sequence as herein indicated is provided. Within the cell, the nucleotide sequence may be incorporated within the chromosome or may be extra-chromosomal. There may be more than one heterologous nucleotide sequence per haploid genome. This, for example, enables increased expression of the gene product compared with endogenous levels, as discussed below. A nucleic acid sequence comprised within a plant cell may be placed under the control of an externally inducible gene promoter, either to place expression under the control of the user or to provide for expression in response to stress.

A nucleic acid which is stably incorporated into the genome of a plant is passed from generation to generation to descendants of the plant, cells of which descendants may express the encoded flavoprotein polypeptide and so may have enhanced stress or pathogen tolerance.

A plant cell may contain a nucleic acid sequence encoding a flavoprotein polypeptide as a result of the introduction of the nucleic acid sequence into an ancestor cell.

In some embodiments, the flavoprotein polypeptide may be expressed within the plant cell as part of a fusion polypeptide which also comprises a chloroplast targeting peptide.

A plant cell as described herein may be comprised in a plant, a plant part or a plant propagule, or an extract or derivative of a plant as described below.

Plants which include a plant cell as described herein are also provided, along with any part or propagule thereof, seed, selfed or hybrid progeny and descendants. Particularly provided are transgenic higher plants, especially crop plants, which have been engineered to carry genes identified as stated above. Examples of suitable plants include tobacco, cucurbits, carrot, vegetable brassica, melons, capsicums, grape vines, lettuce, strawberry, oilseed brassica, sugar beet, wheat, barley, maize, rice, soyabeans, peas, sorghum, sunflower, tomato, potato, pepper, chrysanthemum, carnation, poplar, eucalyptus and pine.

A plant according to the present invention may be one which does not breed true in one or more properties. Plant varieties may be excluded, particularly registrable plant varieties according to Plant Breeders Rights. It is noted that a plant need not be considered a "plant variety" simply because it contains stably within its genome a transgene, introduced into a cell of the plant or an ancestor thereof.

In addition to a plant, the present invention provides any clone of such a plant, seed, selfed or hybrid progeny and descendants, and any part or propagule of any of these, such as cuttings and seed, which may be used in reproduction or propagation, sexual or asexual. Also encompassed by the invention is a plant which is a sexually or asexually propagated off-spring, clone or descendant of such a plant, or any part or propagule of said plant, off-spring, clone or descendant.

The present invention also encompasses the polypeptide expression product of a nucleic acid molecule according to the invention as disclosed herein. Such an isolated polypeptide may consist of a fusion polypeptide which comprises or consists of a flavoprotein polypeptide and a chloroplast targeting peptide, for example a fusion polypeptide which comprises or consists of a flavodoxin polypeptide and a chloroplast targeting peptide. The chloroplast targeting peptide may be heterogeneous to i.e. foreign or not normally or naturally associated with the flavoprotein polypeptide.

A preferred polypeptide includes the amino acid sequence shown in FIG. 4. Such a fusion polypeptide may be encoded by a nucleic acid sequence as described herein, for example the nucleic acid sequence shown in FIG. 3.

Also provided are methods of making such an expression product by expression from a nucleotide sequence encoding therefore under suitable conditions in suitable host cells e.g. E. coli. Those skilled in the art are well able to construct vectors and design protocols and systems for expression and recovery of products of recombinant gene expression.

The invention further provides a method of enhancing improving or increasing the stress tolerance of a plant which includes expressing a nucleic acid sequence encoding a flavoprotein polypeptide (i.e. causing or allowing transcription from a nucleic acid) within cells of the plant.

Suitable flavoprotein polypeptides include FNR polypeptides and flavodoxin polypeptides as described herein.

Improved stress tolerance may include enhanced or increased tolerance to environmental stresses such as ultraviolet UV radiation, extreme temperatures, irradiation, and/or pathogen infection, for example bacterial or fungal infection, in particular necrotizing pathogens, relative to normal, untreated plants.

The ability of a plant to tolerate stress may be increased by expression from a nucleotide sequence encoding a flavoprotein polypeptide such as a flavodoxin polypeptide within cells of a plant (thereby producing the encoded polypeptide), following an earlier step of introduction of the nucleotide sequence into a cell of the plant or an ancestor thereof. Such a method may raise the plants tolerance to stress and/or resistance to pathogen.

Preferably such a method includes causing or allowing the accumulation of the flavoprotein polypeptide within the chloroplasts of said cells, for example by expressing the nucleic acid within the chloroplasts of said cells or providing for the transport of the expressed protein into the chloroplasts. The level of flavoprotein in chloroplasts is increased or enhanced over the normal, endogenous levels of the flavoprotein as a result of such expression.

In some embodiments, chloroplast accumulation is achieved by expressing a fusion protein which comprises the flavodoxin polypeptide and a chloroplast targeting peptide.

Control experiments may be performed as appropriate in the methods described herein. The performance of suitable controls is well within the competence and ability of a skilled person in the field.

The disclosures of all documents mentioned herein are incorporated herein by reference.

Various further aspects and embodiments of the present invention will be apparent to those skilled in the art in view of the present disclosure.

Certain aspects and embodiments of the invention will now be illustrated by way of example and with reference to the figure described below,

BRIEF DESCRIPTION OF THE FIGURES AND TABLES

FIG. 1 shows that flavodoxin expression increases resistance to methyl viologen toxicity in transgenic tobacco plants.

FIG. 2 shows a scheme of the binary vector pCAMBIA 2200 containing a fragment of the in-frame fusion between the sequences encoding pea FNR transit peptide and the flavodoxin gene. The cassette inserted in the Eco RI site of the pCAMBIA 2200 was previously constructed in pDH51. This Eco RI fragment contained the CaMV 35S promoter, the flavodoxin chimeric gene and the CaMV35S polyadenylation signal.

FIG. 3 shows the nucleotide sequence of the in-frame fusions of the pea FNR transit peptide with the flavodoxin gene (SEQ ID NO:1). The initiation codon (ATG) of the transit peptide and the initial codon of flavodoxin (ATG) are indicated in bold, and the stop codon (TAA) is underlined.

Figure 4:
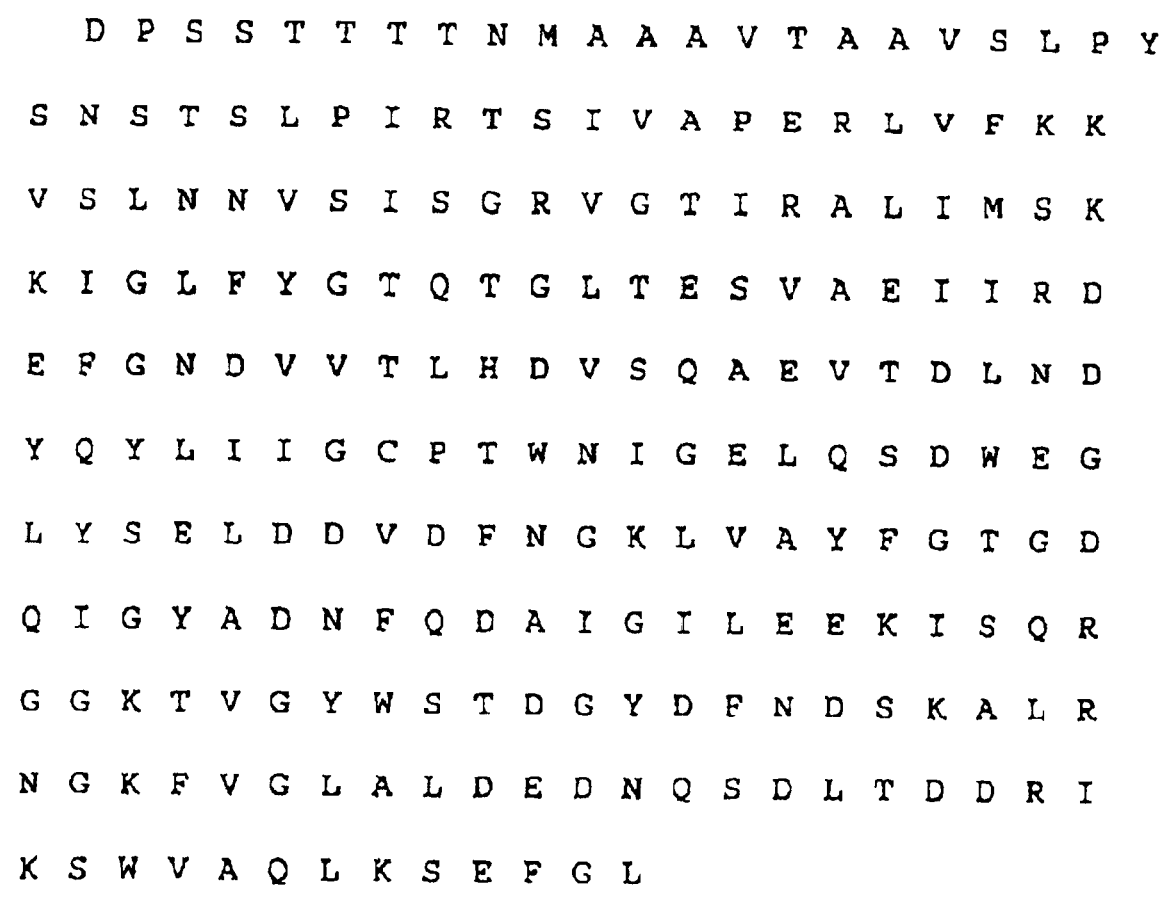

FIG. 4 shows the predicted protein sequence of the transit peptide and flavodoxin protein (SEQ ID NO:2).

FIG. 5 shows the nucleic acid sequences of the chloroplast transit peptide of pea FNR (SEQ ID NO:3).

FIG. 6 shows the amino acid sequence of the chloroplast transit peptide of pea FNR (SEQ ID NO:4).

Figure 1:
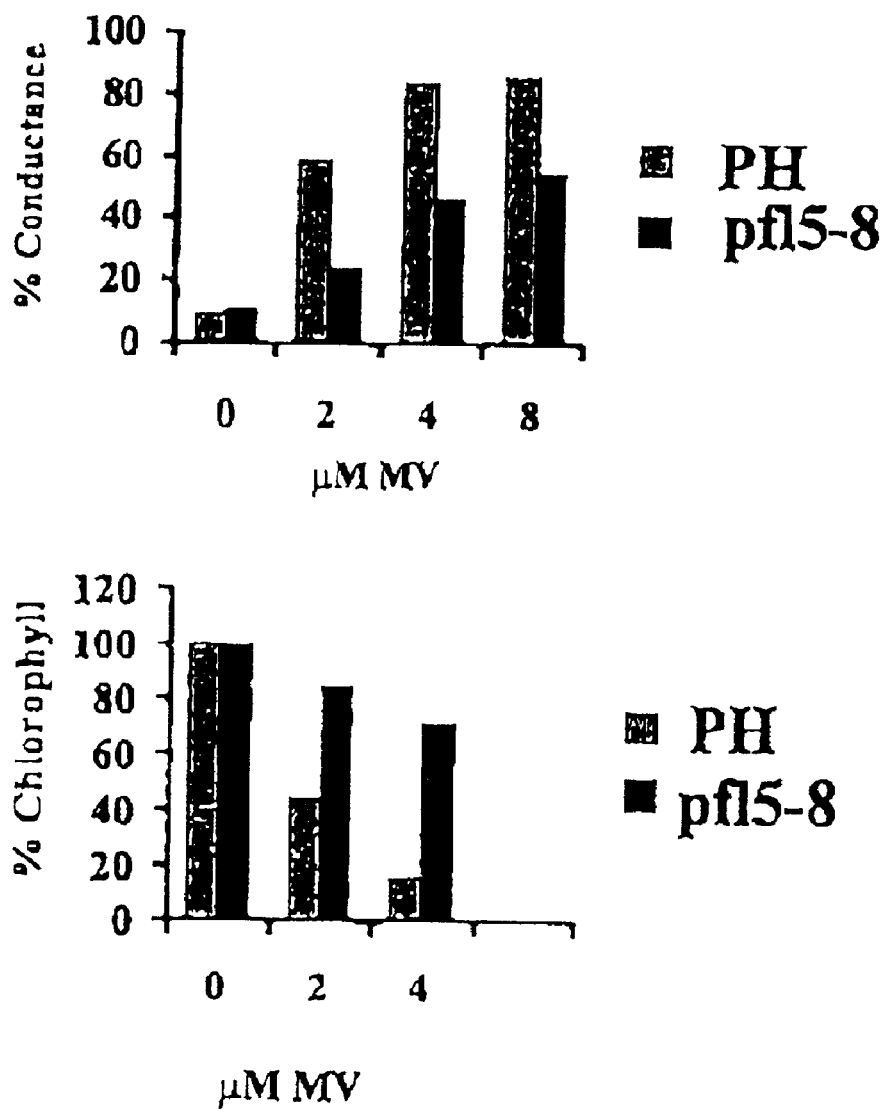
Figure 2:
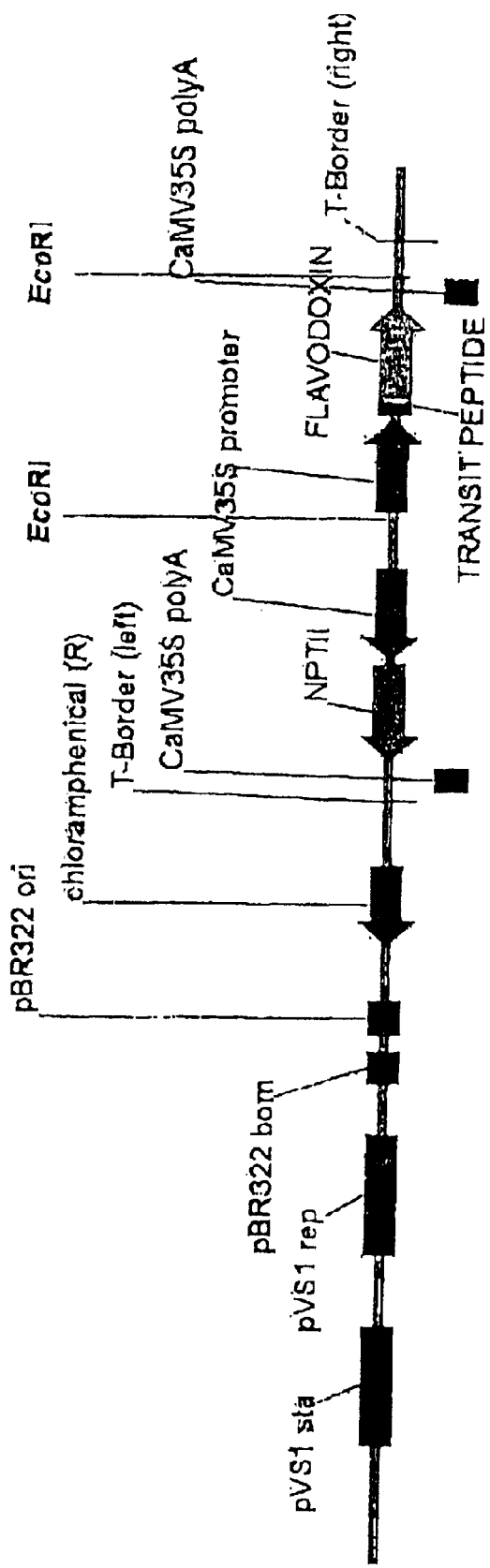

Table 1 shows the database details of known flavodoxin genes from a variety of microbes.

Table 2 shows the database details of known chloroplast targeting peptides.

Experimental

Materials and Methods

Construction of Ti Vectors for Flavodoxin Expression

A DNA fragment encoding Anabaena PCC7119 flavodoxin was obtained by PCR amplification of the cloned gene (Fillat, M. F. et al(1991) Biochem. J. 280, 187–191) from primers 5'-GACGAGCTCTCATA<u>AT</u>GTCAAAG-3' (SEQ ID NO:5), and; 5'-ACTGTCGACTTT<u>TT</u>ACAAACCAAAT-3' (SEQ ID NO:6), complementary to positions-14 to 9 and 515 to 540, respectively.

To facilitate further manipulations, a SacI recognition site (GAGCTC) was introduced in the 5' end primer and a SalI site (GTCGAC) in the 3' end primer The PCR conditions were 30 cycles of 60 s at 94° C., 90 s at 52° C. and 90 s at 72° C., using 1 ng of template DNA and 50 pmol of each primer in a medium containing 10 mM Tris-HCl pH 8.4, 5 mM KCl, 1.5 MM $MgCl_2$, 0.2 mM of each dNTP and 5 units of Taq DNA polymerase. After the 30 cycles were completed, the reactions were incubated at 72° C. for 10 min. A purified PCR fragment of the predicted length (540 bp) was digested with SacI and SalI. The fragment was cloned into compatible sites of a pUC9-derived recombinant plasmid encoding the entire FNR precursor (Ceccarelli, E. A. et al (1991) J. Biol. Chem. 266, 14283–14287) between BamHI and SalI restriction sites, and from which a DNA fragment encoding the mature region of pea FNR had been removed by digestion with SacI and SalI. This generated an in-frame fusion of the chloroplast transit peptide derived from FNR with the flavodoxin protein.

The sequence of the chimeric gene was determined on both strands, and excised from the corresponding plasmid by digestion with BamHI and SalI. The 710-bp fragment was then cloned between the CaMV 35S promoter and polyadenylation regions of pDH51 (Pietrzcak, M. et al (1986) Nucleic Acids Res. 14, 5857–5868). The entire cassette was further isolated as an EcoRI fragment and inserted into the EcoRI site of the binary vector pCAMBIA 2200 (Hajdukiewiez, P. et al (1994) Plant Mol Biol. 25, 989–994). The construct was finally mobilized into *Agrobacterium tumefasciens* strain LBA 4404 by electroporation (Ausubel, F. M. et al (1987) Current Protocols in Molecular Cloning. New York, N.Y.: John Wiley and Sons).

Plant Transformation and Characterization

Tobacco leaf disc transformation was carried out using conventional techniques (Gallois, P. and Marinho, P. (1995) Plant gene transfer and expression protocols. In Methods in Molecular Biology (H. Jones, ed.), vol, 49, pp. 39–49. Humana Press Inc., Totowa, N.J.), and the progenies of kanamycin-resistant transformants were analyzed further. The presence of the flavodoxin gene in the transgenic lines was evaluated by Southern blot hybridization, using standard procedures. Primary transformants expressing high levels of bacterial flavodoxin, as evaluated by SDS-PAGE and immunoblotting (Krapp, A. R. et al (1997) Eur. J. Biochem. 249, 556–563), were self-pollinated and all subsequent experiments were carried out with the homozygous progeny.

Seeds of control and transgenic plants were germinated on Murashige-Skoog (MS) solid medium supplemented with 2% (w/v) sucrose and, in the case of transformants, 100 μg $ml^{-1}$ kanamycin. After two weeks at 25° C. and 200 μmol quanta $m^{-2}$ $s^{-1}$ (14 h light/10 h dark), seedlings were transplanted to fresh MS medium in Magenta vessels. When required, four-week old plantlets were placed on soil or grown hydroponically in nutrient medium (Geiger, M. et al. (1999) Plant Cell Environ. 22, 1177–1199). MV was included in the watering solution. Leaf discs of 12 mm diameter were punched from young fully expanded leaves of two-month old tobacco plants grown on soil. Discs were weighted and floated individually, top side up, on 1 ml sterile distilled water containing the indicated amounts of MV in 24-well plates, infiltrated in vacuum, and incubated in the dark for 2 h at 25° C. to allow diffusion of the MV into the leaf. Wells were illuminated with a white light source at 500 μmol quanta $m^{-2}$ $s^{-1}$. Controls were kept in the dark. Electrolyte leakage of the leaf discs during Mv stress was measured as conductivity of the medium with an Horiba model B-173 conductivity meter.

To evaluate the tolerance of flavodoxin-expressing transformants to extreme temperatures, two-week old plantlets were exposed to 500 μmol quanta $m^{-2}$ $s^{-1}$ plantlets at either 8° C. or 40° C. for 12 h. Light treatments were carried out on four-week old plants, by focusing a light beam (B cm diameter) of 2000 μmol quanta $m^{-2}$ $s^{-1}$ on the upper surface of the third or fourth fully expanded leaf with the aid of a light cannon for 18 h at at 25° C. Tolerance to ultraviolet AB radiation was assayed by exposing four-week old plants to a combination of UV-A (315–400 nm at 2.2 W $m^{-2}$), UV-B (250–315 nm at 1.0 W $m^{-2}$) and photosynthetic active radiation (67 μmol quanta $m^{-2}$ $s^{-1}$) for 24 h at 25° C. The UV lamps were wrapped in cellulose acetate foil (0,076 mm thick) to screen out any UV-C radiation (<280 nm). UV intensities were measured with UV-AB radiometer (Macam photometric LTD, Scotland).

Exposure to Plant Pathogens

*X campestris* pv. *vesicatoria* cells were grown to $OD_{600}$-1.3 in PYDAC medium (Vernière, C. et al (1991) Fruits 46, 162–170). The third and fourth leaves above hypocotyl from eight-week old control and transgenic tobacco plants were inoculated with a suspension of these bacteria in 0.85% (w/v) NaCl.

Isolates from *Alternaria alternata* strain CEREMIC 1333 were grown for six days in potato dextrose agar. Exposure of tobacco leaves to the pathogen was carried out using two different methods. In one of the procedures, discs of 7 mm were excised from fungal cultures and layered on the surface of cut leaves placed on 1.5% (w/v) agar in Petri dishes. Plates were incubated at 25° C. essentially as described by Deák et al. (Deák, M. et al. (1999) Nature Biotechnol. 17, 192–196). Alternatively, conidia from a saturated culture were re-suspended in 500 $\mu$l of sterile distilled water and infiltrated on the upper surface of the corresponding leaves with the aid of a needle-less syringe.

In all cases, symptoms were evaluated by estimating the diameters of necrotized leaf areas.

Analytical Procedures

Carbon dioxide assimilation in response to changes in incident PPFD were measured on the second fully expanded leaf of 4 four-week old transgenic and control plants, using a Qubit Systems Inc. infra-red gas analyzer (IRGA) Package (Kingston, Canada). Chlorophyll contents in leaves and plastids were determined using standard methods (Lichtenthaler, H. K. (1987) Methods Enzymol. 148, 350–382).

Results

Expression of Anabaena PCC 7119 Flavodoxin in Transgenic Tobacco Chloroplasts

To express cyanobacterial flavodoxin in tobacco plastids, a chimeric gene was prepared in which the flavodoxin coding region (Fillat, M. F. et al (1991) Biochem. J. 280, 187–191) was fused in-frame to DNA sequence encoding the chloroplast transit peptide of pea FNR (Newman, B. J., and Gray, J. C. (1988) Plant Mol. Biol. 10, 511–520) (for details, see Methods). The construct was cloned into an Agrobacterium binary vector under the control of the constitutive CaMV 35S gene promoter, and delivered into tobacco cells via Agrobacterium-mediated leaf disc transformation.

Kanamycin-resistant plants were recovered from tissue culture and evaluated for flavodoxin accumulation by immunoblotting.

Proteins extracted from sampled primary transformants (pfl5-pfl12) or from a wild-type tobacco specimen (PH) were resolved by SDS-PAGE, and either stained with Coomassie Brilliant Blue, or blotted onto nitrocellulose membranes and probed with antisera raised against Anabaena PCC7119 flavodoxin using standard techniques (Krapp, A. R. et al. (1997) supra). Proteins corresponding to 16 mm$^2$ of foliar tissue were loaded onto each lane of the gel. Typical homozygous (pfl5-8 and pfl5-6), heterozygous (pfl5-7) and segregant (pfl5-22) plants were recognised based on their flavodoxin contents.

A mature-sized reactive band could be detected at various levels in leaf extracts obtained from several transformants, suggesting plastid import and processing of the expressed flavoprotein. Immunodetection of flavodoxin in purified chloroplast fractions from transformed plants confirmed that the bacterial protein was targeted to plastids.

Primary transformants displaying high levels of flavodoxin expression, and containing a single transgene insertion locus per genome as assessed by Southern blot hybridization, were selfed, and homozygous lines were further selected by flavodoxin dosage.

Chloroplast-Targeted Bacterial Flavodoxin Promotes Tolerance to Methyl Viologen Toxicity in Transgenic Tobacco Two-week old transgenic (pfl5-8) or wild-type (PH) plantlets were cultured on MS agar broth containing 15 $\mu$M or 30 $\mu$M MV and illuminated at 300 $\mu$mol quanta m$^{-2}$ s$^{-1}$ for 24 h at 25° C. Four-week old plants grown under hydroponic conditions were exposed to 30 $\mu$M MV in the nutrient solution, using the incubation time and light regime reported above.

Two-week old plantlets expressing flavodoxin were observed to survive treatment with 30–50 $\mu$M of the superoxide radical propagator MV in illuminated agar plates, whereas non-transformed tobacco controls were extensively bleached under the same conditions. Four week old plants were more tolerant to MV, but significant differences were still evident between transgenic plants and their wild-type siblings (FIG. 1).

Experiments were performed to show the tolerance of flavodoxin-proficient leaf discs to MV as described above. Leaf tissue bleaching was perceived visually in the control discs, reflecting increased chlorophyll degradation. Conductance values were corrected for ion leakage occurring in the dark under the same conditions. The ion leakage values of each sample were expressed as a percentage of the total ion content (maximal value obtained after autoclaving the leaf disks at the end of the MV treatment). Chlorophyll contents were expressed as the fraction of the total chlorophyll content of leaf disks incubated under the same conditions in the absence of Mv. The heights of the vertical bare represent the averages of four experiments with SE lower than 15% (FIG. 1).

Over-production of flavodoxin was observed to provide protection against MV-induced ion leakage (which is indicative of cell membrane deterioration) and bleaching of leaf discs from two-month old plants. In all cases, the extent of damage decreased as the levels of chloroplastic flavodoxin were raised.

Flavodoxin Protects Tobacco Plants against Extreme Temperatures and Irradiation

Transformants of the $F_1$ generation (pfl5-8) and their wild-type siblings (PH) were exposed to 40° C., high fluence rates, or ultraviolet UV-AB radiation, as described under Methods. Four-week old plants were used in all cases, except for the heating experiments, in which two-week old specimens were employed.

To investigate differences in chilling sensitivity of wild-type and flavodoxin-expressing tobacco plants, seeds of control and transgenic plants were germinated on MS solid medium supplemented with 2% (w/v) sucrose for two weeks at 25° C. and 200 $\mu$mol quanta m$^{-2}$ s$^{-1}$ (14 h light/10 h dark). Seedlings were transferred to 9° C. under the same light regime for other two weeks allowing plants to acclimate. Thereafter, they were continuously illuminated (500 $\mu$mol quanta m$^{-2}$ s$^{-1}$) for one more week at 9° C.

To investigate water-deficit tolerance of transgenic tobacco expressing flavodoxin, plants were grown for two weeks in MS as described above and then transferred to soil and daily irrigated with nutrient solution The water-deficit stress was applied to two month-old plants by withholding water for up to 3 days. All other growing conditions were the same as described in Methods Transformants exhibited increased tolerance to this drought regime, whereas damage in control plants was reflected by extensive leaf withering and/or bleaching, with concomitant decreases in chlorophyll contents and photosynthetic capacities.

Young tobacco plantlets accumulating flavodoxin were found to survive prolonged illumination (500 $\mu$mol quanta m$^{-2}$ s$^{-1}$ for 12 h) at 40° C. and exhibited increased tolerance to chilling. Under similar conditions, wild-type control seedlings were severely damaged.

Exposure of the plants to ultraviolet AB (UV-AB) radiation, extremely high light intensities or water deficiency yielded essentially the same results as above.

The damage caused by these treatments in control tobacco plants was reflected by extensive bleaching of the leaf tissue, with concomitant decreases in chlorophyll contents and photosynthetic capacities.

Reduced Damage in Tobacco Transformants Expressing Flavodoxin Exposed to Necrotrophic Pathogens Control and flavodoxin-expressing tobacco plants, grown in the greenhouse for eight weeks were inoculated with a suspension of the pathogenic bacterium *Xanthomonas campestris* pv. *vesicatoria*, known to induce the hypersensitive response in tobacco (Baker, C. J., and Orlandi, E. W. (1995) Ann. Rev. Phytopathol. 33, 299–321). The number of necrotic symptoms was drastically reduced in transformants expressing the cyanobacterial protein, with a negative correlation between the extent of damage and the flavodoxin levels accumulated in the corresponding tissue.

Fungal infection with *A. alternata* was done using two different procedures. Firstly, discs of 7 mm excised from fungal cultures were layered on the surface of cut leaves placed on 1.5% (w/v) agar in Petri dishes. Plates were incubated at 25° C. essentially as described by Deák et al (Deák et al (1999) supra) for 10 days. Secondly, a disc of filter paper imbibed in conidia from a saturated culture (around 20,000 conidia) was placed on the upper surface of the corresponding leaves. Symptoms on the leaves were observed after 18 days of fungal infection.

Transgenic plants were observed to be more tolerant than their wild-type siblings to necrosis induced by infection with the pathogenic fungus *Alternaria alternata*.

To investigate necrotization of tobacco wild-type and transgenic leaves after infection by tobacco necrotic virus, plants were planted in soil and grown for three weeks at 25° C. and 300 μmol quanta m$^{-2}$ s$^{-1}$ with 14 h light/10 h dark as described in Methods, The third leaves position above hypocotyl were inoculated with a suspension of the tobacco necrotic virus, with an abrasive and kept under the same growing conditions. Lesions were examined after one week of inoculation.

Transgenic plants were observed to be more tolerant than their wild-type siblings to necrosis induced by infection with the tobacco necrotic virus.

Expression of flavodoxin in plant cells was thus observed to protect transgenic plants against pathogens that cause necrotic lesions.

TABLE 1

| Accession No. | | Gene | Species |
|---|---|---|---|
| NP_358768 | gi\|15903218 | Flavodoxin | Streptococcus pneumoniae R6 |
| NP_345761 | gi\|15901157 | Flavodoxin | Streptococcus pneumoniae TIGR4 |
| NP_311794 | gi\|15833021 | flavodoxin 2 | Escherichia coli O157:H7] |
| NP_311593 | gi\|15832820 | putative flavodoxin | Escherichia coli O157:H7 |
| NP_308742 | gi\|15829969 | flavodoxin 1 | Escherichia coli O157:H7 |
| CAC92877 | gi\|15980620 | flavodoxin 1 | Yersinia pestis |
| CAC89737 | gi\|15978964 | flavodoxin 2 | Yersinia pestis |
| NP_350007 | gi\|15896658 | Flavodoxin | Clostridium acetobutylicum |
| NP_349066 | gi\|15895717 | Flavodoxin | Clostridium acetobutylicum |
| NP_347225 | gi\|15893876 | Flavodoxin | Clostridium acetobutylicum |
| NP_346845 | gi\|15893496 | Flavodoxin | Clostridium acetobutylicum |
| NP_348645 | gi\|15895296 | Predicted flavodoxin | Clostridium acetobutylicum |
| NP_347225 | gi\|15893876 | Flavodoxin | Clostridium acetobutylicum |
| NP_346845 | gi\|15893496 | Flavodoxin | Clostridium acetobutylicum |
| NP_282528 | gi\|15792705 | Flavodoxin | Campylobacter jejuni |
| AAK28628 | gi\|13507531 | Flavodoxin | Aeromonas hydrophila |
| NP_268951 | gi\|15674777 | putative flavodoxin | Streptococcus pyogenes |
| NP_266764 | gi\|15672590 | Flavodoxin | Lactococcus lactis subsp. lactis |
| NP_207952 | gi\|15645775 | flavodoxin (fldA) | Helicobacter pylori 26695 |
| NP_232050 | gi\|15642417 | flavodoxin 2 | Vibrio cholerae |
| NP_231731 | gi\|15642099 | flavodoxin 1 | Vibrio cholerae |
| NP_219360 | gi\|15639910 | Flavodoxin | Treponema pallidum |
| NP_24012 | gi\|15616909 | flavodoxin 1 | Buchnera sp. APS |
| NP_214435 | gi\|15607053 | Flavodoxin | Aquifex aeolicus |
| FXAVEP | gi\|625194 | flavodoxin | Azotobacter vinelandii |
| S38632 | gi\|481443 | flavodoxin | -Synechocystis sp. (strain PCC 6803) |
| FXDV | gi\|476442 | flavodoxin | Desulfovibrio vulgaris |
| A34640 | gi\|97369 | flavodoxin | Desulfovibrio salexigens |
| S24311 | gi\|97368 | flavodoxin | Desulfovibrio gigas (ATCC 19364) |
| A37319 | gi\|95841 | flavodoxin A | Escherichia coli |
| S06648 | gi\|81145 | flavodoxin | red alga (Chondrus crispus) |
| S04600 | gi\|79771 | flavodoxin | Anabaena variabilis |
| A28670 | gi\|79632 | flavodoxin | Synechococcus sp |
| S02511 | gi\|78953 | flavodoxin | Klebsiella pneumoniae |
| FXDVD | gi\|65884 | flavodoxin | Desulfovibrio desulfuricans (ATCC 29577) |
| FXCLEX | gi\|65882 | flavodoxin | Clostridium sp |
| FXME | gi\|65881 | flavodoxin | Megasphaera elsdenii |
| NP_071157 | gi\|11499913 | flavodoxin, putative | Archaeoglobus fulgidus |
| BAA17947 | gi\|1653030 | flavodoxin | Synechocystis sp. PCC 6803 |
| BAB61723 | gi\|14587807 | flavodoxin 2 | Vibrio fischeri |
| BAB61721 | gi\|14587804 | flavodoxin 1 | Vibrio fischeri |
| AAK66769 | gi\|14538018 | flavodoxin | Histophilus ovis |
| P57385 | gi\|11132294 | FLAVODOXIN | |
| AAC7593 | gi\|1789262 | flavodoxin 2 | Escherichia coli K12 |
| AAC73778 | gi\|1786900 | flavodoxin 1 | Escherichia coli K12 |
| AAC75752 | gi\|1789064 | putative flavodoxin | Escherichia coli K12 |
| F69821 | gi\|7429905 | flavodoxin homolog yhcB | Bacillus subtilis |
| QQKBFP | gi\|2144338 | pyruvate (flavodoxin) dehydrogenase nifJ | Klebsiella pneumoniae |
| S16929 | gi\|95027 | flavodoxin A | Azotobacter chroococcum |
| F71263 | gi\|7430914 | probable flavodoxin | Syphilis spirochete |
| A64665 | gi\|7430911 | flavodoxin | Helicobacter pylori (strain 26695 |
| JE0109 | gi\|7430907 | flavodoxin | Desulfovibrio vulgaris |
| S42570 | gi\|628879 | flavodoxin | Desulfovibrio desulfuricans (ATCC 27774) |
| BAB13365 | gi\|10047146 | flavodoxin | Alteromonas sp. O-7 |
| AAF34250 | gi\|6978032 | flavodoxin | Desulfovibrio gigas |
| CAB73809 | gi\|6968816 | flavodoxin | Campylobacter jejuni |
| D69541 | gi\|7483302 | flavodoxin homolog | Archaeoglobus fulgidus |
| F70479 | gi\|7445354 | flavodoxin | Aquifex aeolicus |
| S55234 | gi\|1084290 | flavodoxin isoform I | Chlorella fusca |
| S18374 | gi\|2117434 | flavodoxin | Anabaena sp. (PCC 7119) |
| S55235 | gi\|1084291 | flavodoxin isoform II | Chlorella fusca |
| C64053 | gi\|1074088 | flavodoxin A | Haemophilus influenzae (strain Rd KW20) |
| A61338 | gi\|625362 | flavodoxin | Clostridium pasteurianum |
| A39414 | gi\|95560 | flavodoxin | Enterobacter agglomerans plasmid pEA3 |
| AAD08207 | gi\|2314319 | flavodoxin (fldA) | Helicobacter pylori 26695 |
| CAB37851 | gi\|4467982 | flavodoxin | Rhodobacter capsulatus |
| AAC65882 | gi\|3323245 | flavodoxin | Treponema pallidum |
| AAB88920 | gi\|2648181 | flavodoxin, putative | Archaeoglobus fulgidus |
| AAB65080 | gi\|2289914 | flavodoxin | Klebsiella pneumoniae |
| AAB53659 | gi\|710356 | flavoprotein | Methanothermobacter thermautotrophicus |
| AAB51076 | gi\|1914879 | flavodoxin | Klebsiella pneumoniae |
| AAB36613 | gi\|398014 | flavodoxin | Azotobacter chroococcum |
| AAB20462 | gi\|239748 | flavodoxin | Anabaena |
| AAA64735 | gi\|142370 | flavodoxin (nifF) | Azotobacter vinelandii |
| BAA35341 | gi\|1651296 | Flavodoxin | Escherichia coli |
| BAA35333 | gi\|1651291 | Flavodoxin | Escherichia coli |
| AAA27288 | gi\|415254 | flavodoxin | Synechocystis sp. |
| AAA27318 | gi\|154528 | Flavodoxin | Synechococcus sp. |
| AAC45773 | gi\|1916334 | putative flavodoxin | Salmonella typhimurium |
| AAC07825 | gi\|2984302 | flavodoxin | Aquifex aeolicus |
| AAC02683 | gi\|2865512 | flavodoxin | Trichodesmium erythraeum |

TABLE 2

| Accession No | Gene | | Species |
|---|---|---|---|
| P32260 | gi\|12644209 | CYSTEINE SYNTHASE, CHLOROPLAST PRECURSOR | Spinacia oleracea |
| AAG59996 | gi\|12658639 | ferredoxin:sulfite reductase precursor | Glycine max |
| S10200 | gi\|100078 | carbonate dehydratase precursor | Pisum sativum |
| CAB89287 | gi\|7672161 | chloroplast FtsZ-like protein | Nicotiana tabacum |
| P17067 | gi\|115471 | CARBONIC ANHYDRASE, CHLOROPLAST PRECURSOR (CARBONATE DEHYDRATASE) | Pisum sativum |
| AAD22109 | gi\|4530595 | heme oxygenase 2 | Arabidopsis thaliana |
| AAD22108 | gi\|4530593 | heme oxygenase 1 | Arabidopsis thaliana |
| AAC50035 | gi\|450235 | APS kinase | Arabidopsis thaliana |
| AAC12846 | gi\|1051180 | phytoene desaturase | Zea mays |
| AAB87573 | gi\|2645999 | chlorophyll a/b binding protein of LHCII type I precursor | Panax ginseng |
| CAA47329 | gi\|312944 | cysteine synthase | Spinacia oleracea |
| CAA31137 | gi\|141201 | O-acetylserine sulfhydrylase | Escherichia coli |
| AAA82068 | gi\|1079732 | cpFtsZ | Arabidopsis thaliana |
| T06368 | gi\|7489040 | photosystem II oxygen-evolving complex protein 1 precursor | Lycopersicon esculentum |
| S71750 | gi\|7488813 | import intermediate-associated 100K protein precursor | Pisum sativum |
| S71749 | gi\|7459239 | DCL protein precursor, chloroplast | Lycopersicon esculentum |
| 15825883 | gi\|15825883 | Chain B, Structure Of Threonine Synthase | Arabidopsis thaliana |
| 15825882 | gi\|15825882 | Chain A, Structure Of Threonine Synthase | Arabidopsis thaliana |
| T09543 | gi\|7488970 | deoxyxylulose synthase TKT2 precursor | Capsicum annuum |
| JC5876 | gi\|7447856 | early light-inducible protein precursor | Glycine max |
| P24493 | gi\|1170215 | DELTA-AMINOLEVULINIC ACID DEHYDRATASE PRECURSOR | Spinacia oleracea |
| S47966 | gi\|1076532 | probable lipid transfer protein M30 precursor | Pisum sativum |
| A44121 | gi\|322404 | ribosomal protein S1 precursor | Spinacia oleracea |
| S01056 | gi\|81896 | early light-induced protein precursor | Pisum sativum |
| O22773 | gi\|7388292 | THYLAKOID LUMENAL 16.5 KDA PROTEIN, CHLOROPLAST PRECURSOR | Arabidopsis thaliana |
| P80470 | gi\|6093830 | PHOTOSYSTEM II CORE COMPLEX PROTEINS PSBY PRECURSOR | Spinacia oleracea |
| P55195 | gi\|1709930 | PHOSPHORIBOSYL-AMINOIMIDAZOLE CARBOXYLASE, CHLOROPLAST PRECURSOR | Vigna aconitifolia |
| P11970 | gi\|1709654 | PLASTOCYANIN B, CHLOROPLAST PRECURSOR | Populus nigra |
| P00299 | gi\|1709651 | PLASTOCYANIN A, CHLOROPLAST PRECURSOR | Populus nigra |
| P80484 | gi\|1709608 | PERIDININ-CHLOROPHYLL A PROTEIN 1 PRECURSOR | Amphidinium carterae |
| P08823 | gi\|134102 | RUBISCO SUBUNIT BINDING-PROTEIN ALPHA SUBUNIT PRECURSOR | Triticum aestivum |
| P04045 | gi\|130173 | ALPHA-1,4 GLUCAN PHOSPHORYLASE, L-1 ISOZYME, CHLOROPLAST PRECURSOR | Solanum tuberosum |
| S30897 | gi\|7427677 | 3-isopropylmalate dehydrogenase precursor | Solanum tuberosum |
| TXSPM | gi\|7427615 | thioredoxin m precursor | Spinacia oleracea |
| FEKM | gi\|7427604 | ferredoxin [2Fe-2S] precursor | Chlamydomonas reinhardtii |
| CCKM6R | gi\|2144284 | cytochrome c6 precursor | Chlamydomonas reinhardtii |
| S30145 | gi\|419757 | ketol-acid reductoisomerase precursor | Arabidopsis thaliana |
| DEMZMC | gi\|319840 | malate dehydrogenase (NADP+) precursor | Zea mays |
| S20510 | gi\|81676 | 3-isopropylmalate dehydrogenase precursor | Brassica napus |
| S17180 | gi\|81509 | ketol-acid reductoisomerase precursor | Spinacia oleracea |
| Q9SEL7 | gi\|15214049 | PROTEASE HHOA, CHLOROPLAST PRECURSOR | Arabidopsis thaliana |
| O23403 | gi\|13959580 | THYLAKOID LUMENAL 21.5 KDA PROTEIN, CHLOROPLAST PRECURSOR | Arabidopsis thaliana |
| P82281 | gi\|12644689 | PUTATIVE L-ASCORBATE PEROXIDASE, CHLOROPLAST PRECURSOR | Arabidopsis thaliana |
| O22609 | gi\|9910645 | PROTEASE DO-LIKE, CHLOROPLAST PRECURSOR | Arabidopsis thaliana |
| P48417 | gi\|1352186 | ALLENE OXIDE SYNTHASE, CHLOROPLAST PRECURSOR | Linum usitatissimum |
| P49080 | gi\|1351905 | BIFUNCTIONAL ASPARTOKINASE/HOMOSERINE DEHYDROGENASE 2, CHLOROPLAST PRECURSOR | Zea mays |
| P31853 | gi\|461595 | ATP SYNTHASE B' CHAIN, CHLOROPLAST PRECURSOR | Spinacia oleracea |
| P10933 | gi\|119905 | FERREDOXIN--NADP REDUCTASE, LEAF ISOZYME PRECURSOR | Pisum sativum |
| P52422 | gi\|14917033 | PHOSPHORIBOSYL-GLYCINAMIDE FORMYLTRANSFERASE, CHLOROPLAST PRECURSOR | Arabidopsis thaliana |
| P49077 | gi\|14917032 | ASPARTATE CARBAMOYLTRANSFERASE PRECURSOR | Arabidopsis thaliana |
| O50039 | gi\|14917022 | ORNITHINE CARBAMOYL-TRANSFERASE, CHLOROPLAST PRECURSOR | Arabidopsis thaliana |

TABLE 2-continued

| Accession No | | Gene | Species |
|---|---|---|---|
| P55229 | gi\|14916987 | GLUCOSE-1-PHOSPHATE ADENYLYLTRANSFERASE LARGE SUBUNIT 1, CHLOROPLAST PRECURSOR | Arabidopsis thaliana |
| Q96291 | gi\|14916972 | 2-CYS PEROXIREDOXIN BAS1, CHLOROPLAST PRECURSOR | Arabidopsis thaliana |
| Q9ZT00 | gi\|14916690 | RIBULOSE BISPHOSPHATE CARBOXYLASE/ OXYGENASE ACTIVASE, CHLOROPLAST PRECURSOR | Zea mays |
| Q9LZX6 | gi\|14547977 | DIHYDRODIPICOLINATE SYNTHASE 1, CHLOROPLAST PRECURSOR | Arabidopsis thaliana |
| O64903 | gi\|12644076 | NUCLEOSIDE DIPHOSPHATE KINASE II, CHLOROPLAST PRECURSOR | Arabidopsis thaliana |
| O04130 | gi\|3122858 | D-3-PHOSPHOGLYCERATE DEHYDROGENASE PRECURSOR | Arabidopsis thaliana |
| O24364 | gi\|3121825 | 2-CYS PEROXIREDOXIN BAS1, CHLOROPLAST PRECURSOR | Spinacia oleracea |
| P49107 | gi\|1709825 | PHOTOSYSTEM I REACTION CENTRE SUBUNIT N PRECURSOR | Arabidopsis thaliana |
| P49132 | gi\|1352199 | TRIOSE PHOSPHATE/PHOSPHATE TRANSLOCATOR, CHLOROPLAST PRECURSOR | Flaveria trinervia |
| P37107 | gi\|586038 | SIGNAL RECOGNITION PARTICLE 54 KDA PROTEIN, CHLOROPLAST PRECURSOR | Arabidopsis thaliana |
| Q04836 | gi\|464662 | 31 KDA RIBONUCLEOPROTEIN, CHLOROPLAST PRECURSOR | Arabidopsis thaliana |
| Q01909 | gi\|461551 | ATP SYNTHASE GAMMA CHAIN 2, CHLOROPLAST PRECURSOR | Arabidopsis thaliana |
| P14671 | gi\|136251 | TRYPTOPHAN SYNTHASE BETA CHAIN 1 PRECURSOR | Arabidopsis thaliana |
| P07089 | gi\|132144 | RIBULOSE BISPHOSPHATE CARBOXYLASE SMALL CHAIN PRECURSOR | Flaveria trinervia |
| P22221 | gi\|130384 | PYRUVATE, PHOSPHATE DIKINASE PRECURSOR | Flaveria trinervia |
| P22178 | gi\|126736 | NADP-DEPENDENT MALIC ENZYME, CHLOROPLAST PRECURSOR | Flaveria trinervia |
| P26259 | gi\|118241 | DIHYDRODIPICOLINATE SYNTHASE, CHLOROPLAST PRECURSOR | Zea mays |
| P23577 | gi\|118044 | APOCYTOCHROME F PRECURSOR | Chlamydomonas reinhardtii |
| Q42522 | gi\|14195661 | GLUTAMATE-1-SEMIALDEHYDE 2,1-AMINOMUTASE 2 PRECURSOR | Arabidopsis thaliana |
| Q96242 | gi\|13878924 | ALLENE OXIDE SYNTHASE PRECURSOR | Arabidopsis thaliana |
| P46312 | gi\|13432148 | OMEGA-6 FATTY ACID DESATURASE, CHLOROPLAST PRECURSOR | Arabidopsis thaliana |
| P34802 | gi\|13432144 | GERANYLGERANYL PYROPHOSPHATE SYNTHETASE, CHLOROPLAST PRECURSOR | Arabidopsis thaliana |
| P50318 | gi\|12644295 | PHOSPHOGLYCERATE KINASE, CHLOROPLAST PRECURSOR | Arabidopsis thaliana |
| P46309 | gi\|12644273 | GLUTAMATE--CYSTEINE LIGASE, CHLOROPLAST PRECURSOR | Arabidopsis thaliana |
| P21276 | gi\|12644157 | SUPEROXIDE DISMUTASE [FE], CHLOROPLAST PRECURSOR | Arabidopsis thaliana |
| O23787 | gi\|6094476 | THIAZOLE BIOSYNTHETIC ENZYME, CHLOROPLAST PRECURSOR | Citrus sinensis |
| P93407 | gi\|3915008 | SUPEROXIDE DISMUTASE [CU-ZN], CHLOROPLAST PRECURSOR | Oryza sativa |
| Q96255 | gi\|3914996 | PHOSPHOSERINE AMINOTRANSFERASE, CHLOROPLAST PRECURSOR | Arabidopsis thaliana |
| O24600 | gi\|3914826 | DNA-DIRECTED RNA POLYMERASE, CHLOROPLAST PRECURSOR | Arabidopsis thaliana |
| O49937 | gi\|3914665 | 50S RIBOSOMAL PROTEIN L4, CHLOROPLAST PRECURSOR | Spinacia oleracea |
| Q42915 | gi\|3914608 | RIBULOSE BISPHOSPHATE CARBOXYLASE SMALL CHAIN PRECURSOR | Manihot esculenta |
| Q39199 | gi\|2500098 | DNA REPAIR PROTEIN RECA, CHLOROPLAST PRECURSOR | Arabidopsis thaliana |
| Q96529 | gi\|2500026 | ADENYLOSUCCINATE SYNTHETASE PRECURSOR | Arabidopsis thaliana |
| P55826 | gi\|2495184 | PROTOPORPHYRINOGEN OXIDASE, CHLOROPLAST PRECURSOR | Arabidopsis thaliana |
| Q42496 | gi\|2493687 | CYTOCHROME B6-F COMPLEX 4 KDA SUBUNIT, CHLOROPLAST PRECURSOR | Chlamydomonas reinhardtii |
| P52424 | gi\|1709925 | PHOSPHORIBOSYL-FORMYLGLY CINAMIDINE CYCLO-LIGASE, CHLOROPLAST PRECURSOR | Vigna unguiculata |
| P49572 | gi\|1351303 | INDOLE-3-GLYCEROL PHOSPHATE SYNTHASE, CHLOROPLAST PRECURSOR | Arabidopsis thaliana |
| P48496 | gi\|1351271 | TRIOSEPHOSPHATE ISOMERASE, CHLOROPLAST PRECURSOR | Spinacia oleracea |
| P25269 | gi\|1174779 | TRYPTOPHAN SYNTHASE BETA CHAIN 2 PRECURSOR | Arabidopsis thaliana |
| P46225 | gi\|1174745 | TRIOSEPHOSPHATE ISOMERASE, CHLOROPLAST PRECURSOR | Secale cereale |
| P46283 | gi\|1173345 | SEDOHEPTULOSE-1,7-BISPHOSPHATASE, CHLOROPLAST PRECURSOR | Arabidopsis thaliana |
| P32069 | gi\|418134 | ANTHRANILATE SYNTHASE COMPONENT I-2 PRECURSOR | Arabidopsis thaliana |
| P29450 | gi\|267120 | THIOREDOXIN F-TYPE, CHLOROPLAST PRECURSOR | Pisum sativum |
| Q9ZTN9 | gi\|13878459 | PHYTOENE DEHYDROGENASE PRECURSOR | Oryza sativa |

TABLE 2-continued

| Accession No | | Gene | Species |
|---|---|---|---|
| Q9SHI1 | gi\|13627881 | TRANSLATION INITIATION FACTOR IF-2, CHLOROPLAST PRECURSOR | Arabidopsis thaliana |
| Q9LR75 | gi\|13431553 | COPROPORPHYRINOGEN III OXIDASE, CHLOROPLAST PRECURSOR | Arabidopsis thaliana |
| Q9ZNZ7 | gi\|12643970 | FERREDOXIN-DEPENDENT GLUTAMATE SYNTHASE 1, CHLOROPLAST PRECURSOR | Arabidopsis thaliana |
| Q9SZ30 | gi\|12643854 | BIFUNCTIONAL HISTIDINE BIOSYNTHESIS PROTEIN HISHF, CHLOROPLAST PRECURSOR | Arabidopsis thaliana |
| Q9SJE1 | gi\|12643848 | MAGNESIUM-CHELATASE SUBUNIT CHLD PRECURSOR | Arabidopsis thaliana |
| Q42624 | gi\|12643761 | GLUTAMINE SYNTHETASE, CHLOROPLAST PRECURSOR | Brassica napus |
| Q38933 | gi\|12643749 | LYCOPENE BETA CYCLASE, CHLOROPLAST PRECURSOR | Arabidopsis thaliana |
| Q42435 | gi\|12643508 | CAPSANTHIN/CAPSORUBIN SYNTHASE, CHLOROPLAST PRECURSOR | Capsicum annuum |

What is claimed is:

1. An isolated nucleic acid encoding a flavodoxin polypeptide fused to a chloroplast targeting peptide.

2. The nucleic acid according to claim 1 wherein the flavodoxin polypeptide is a bacterial flavodoxin.

3. The nucleic acid according to claim 1 wherein the flavodoxin polypeptide is a cyanobacterial flavodoxin.

4. The nucleic acid according to claim 3 wherein the flavodoxin polypeptide is the Anabaena PC7119 flavodoxin polypeptide.

5. The nucleic acid according to claim 1 wherein the chloroplast targeting signal is the chloroplast transit polypeptide of the pea FNR.

6. The nucleic acid according to claim 1 wherein said nucleic acid encodes a fusion polypeptide having the sequence of SEQ ID NO:2.

7. The nucleic acid according to claim 6 wherein the nucleic acid has the nucleotide sequence of SEQ ID NO:1.

8. A nucleic acid vector suitable for transformation of a plant cell comprising the nucleic acid according to claim 1.

9. A transgenic host cell comprising the nucleic acid vector according to claim 8, wherein said host cell is microbial.

10. A transgenic host cell comprising the nucleic acid vector according to claim 8, wherein said host cell is a plant cell.

11. A plant cell comprising a heterogeneous nucleic acid encoding a flavodoxin polypeptide fused to a chloroplast targeting peptide.

12. The plant cell according to claim 11 having said nucleic acid within its genome.

13. The plant cell according to claim 12 having more than one said nucleic acid per haploid genome.

14. The plant cell according to claim 12 which is comprised in a plant, a plant part or a plant propagule.

15. A method of producing the cell according to claim 10, the method comprising incorporating said nucleic acid vector into the cell by means of transformation.

16. The method according to claim 15 wherein said nucleic acid becomes stably incorporated in the cell genome.

17. The method according to claim 13 or claim 16 wherein said method comprises regenerating a plant from one or more transformed cells.

18. A plant comprising the plant cell according to claim 10.

19. A part or propagule of a plant comprising the plant cell according to claim 10.

20. A method of producing a plant, the method comprising incorporating a nucleic acid encoding a flavodoxin polypeptide fused to a chloroplast targeting peptide into a plant cell and regenerating a plant from said plant cell.

21. The method according to claim 20 wherein the nucleic acid is present in a nucleic acid vector.

22. The method according to claim 20 or 21 comprising sexually or asexually propagating off-spring or a descendant of the plant regenerated from said plant cell, wherein said off-spring or descendent comprises said nucleic acid.

23. A method of improving the stress tolerance of a plant, the method comprising introducing a heterogenous nucleic acid encoding a flavodoxin polypeptide fused to a chloroplast targeting peptide into a plant cell, regenerating a plant from said plant cell, and expressing said flavodoxin polypeptide fused to said chloroplast targeting peptide within cells of the plant.

24. The method according to claim 23 wherein said stress is selected from the group consisting of ultraviolet UV radiation, extreme temperatures, irradiation, and pathogen infection.

* * * * *